United States Patent
Roulund et al.

(10) Patent No.: US 9,706,779 B2
(45) Date of Patent: Jul. 18, 2017

(54) TALL FESCUE ENDOPHYTE ISOLATE 647

(71) Applicant: DLF Trifolium A/S, Roskilde (DK)

(72) Inventors: Niels Roulund, Store Heddinge (DK); Anne Mette Dahl Jensen, Aarhus (DK)

(73) Assignee: DLF Trifolium A/S, Roskilde (DK)

( * ) Notice: Subject to any disclaimer, the term of this patent is extended or adjusted under 35 U.S.C. 154(b) by 195 days.

(21) Appl. No.: 14/421,529

(22) PCT Filed: Aug. 23, 2013

(86) PCT No.: PCT/EP2013/067522
§ 371 (c)(1),
(2) Date: Feb. 13, 2015

(87) PCT Pub. No.: WO2014/029862
PCT Pub. Date: Feb. 27, 2014

(65) Prior Publication Data
US 2015/0216180 A1     Aug. 6, 2015

Related U.S. Application Data

(60) Provisional application No. 61/692,810, filed on Aug. 24, 2012.

(51) Int. Cl.
| | | |
|---|---|---|
| *C12N 1/14* | (2006.01) | |
| *A01H 17/00* | (2006.01) | |
| *A01H 5/10* | (2006.01) | |
| *C12R 1/645* | (2006.01) | |
| *A01N 63/04* | (2006.01) | |
| *A01H 5/12* | (2006.01) | |
| *C12Q 1/68* | (2006.01) | |

(52) U.S. Cl.
CPC .............. *A01N 63/04* (2013.01); *A01H 5/12* (2013.01); *C12N 1/14* (2013.01); *C12Q 1/6895* (2013.01); *C12R 1/645* (2013.01); *C12Q 2600/158* (2013.01)

(58) Field of Classification Search
None
See application file for complete search history.

(56) References Cited

U.S. PATENT DOCUMENTS

2005/0150024 A1    7/2005   West et al.

FOREIGN PATENT DOCUMENTS

WO    WO 2004/106487 A2    12/2004
WO    WO 2008/100892 A2    8/2008

OTHER PUBLICATIONS

Jensen et al, 2007, Crop Science, 47:139-147.*
Bouton et al, 2002, Agronomy Journal, 94:567-574.*
Easton, 2007, Euphytica, 154:295-306.*
Pennell et al, 2010, New Zealand Journal of Agricultural Research, 53:145-150.*
Johnson-Cicalese et al., "Cross Species Inoculation of Chewings and Strong Creeping Red Fescues with Fungal Endophytes," *CropSci.* 40:1485-1489, 2000.
Moon et al., "Identification of Epichloë Endophytes in Planta by a Microsatellite-Based PCR Fingerprinting Assay with Automated Analysis," *Appl Environ Microbiol.*65:1268-1279, 1999.
Tapper and Latch, "Selection Against Toxin Production in Endophyte-Infected Perennial Ryegrass," *Grassland Res. Practice Series* No. 7:107-111, 1999.
van Zijll de Jong et al., "Development and Characterization of EST-Derived Simple Sequence Repeat (SSR) Markers for Pasture Grass Endophytes," *Genome* 46:277-290, 2003.

* cited by examiner

*Primary Examiner* — Jason Deveau Rosen
(74) *Attorney, Agent, or Firm* — Klarquist Sparkman, LLP (57) ABSTRACT

This disclosure provides to a new tall fescue grass endophyte (*Neotyphodium coenophialum*) referred to as 647, as well as to synthetic combinations of the 647 endophyte and tall fescue grass plant or tall fescue grass cultivar. This new endophyte does not produce detectable ergovaline or any other ergopeptide alkaloids which are known to be harmful to grazing livestock. Thus, the 647 endophyte can be used in combination with forage grasses. In addition, the 647 endophyte provides increased green matter yield and improved resistance to black beetles (*Heteronychus arator*) and other pests. Thus, the 647 endophyte can be used in combination with grasses susceptible to infection or infestation with black beetles.

13 Claims, 3 Drawing Sheets

SEQUENCE LISTING

```
<160> NUMBER OF SEQ ID NOS: 27

<210> SEQ ID NO 1
<211> LENGTH: 24
<212> TYPE: DNA
<213> ORGANISM: Artificial Sequence
<220> FEATURE:
<223> OTHER INFORMATION: primer for PCR genotyping
```

```
<400> SEQUENCE: 1
cgcacaatac gtcagctagg aatg                                          24

<210> SEQ ID NO 2
<211> LENGTH: 24
<212> TYPE: DNA
<213> ORGANISM: Artificial Sequence
<220> FEATURE:
<223> OTHER INFORMATION: primer for PCR genotyping

<400> SEQUENCE: 2
cctgaatcaa ctttgctatc aggc                                          24

<210> SEQ ID NO 3
<211> LENGTH: 24
<212> TYPE: DNA
<213> ORGANISM: Artificial Sequence
<220> FEATURE:
<223> OTHER INFORMATION: primer for PCR genotyping

<400> SEQUENCE: 3
tggactcgac ttgccctctc tcag                                          24

<210> SEQ ID NO 4
<211> LENGTH: 24
<212> TYPE: DNA
<213> ORGANISM: Artificial Sequence
<220> FEATURE:
<223> OTHER INFORMATION: primer for PCR genotyping

<400> SEQUENCE: 4
tgcgagcagc gtttgcgtgt gcgt                                          24

<210> SEQ ID NO 5
<211> LENGTH: 24
<212> TYPE: DNA
<213> ORGANISM: Artificial Sequence
<220> FEATURE:
<223> OTHER INFORMATION: primer for PCR genotyping

<400> SEQUENCE: 5
aatcgttgtg cgagccattc tggc                                          24

<210> SEQ ID NO 6
<211> LENGTH: 24
<212> TYPE: DNA
<213> ORGANISM: Artificial Sequence
<220> FEATURE:
<223> OTHER INFORMATION: primer for PCR genotyping

<400> SEQUENCE: 6
tccatctccg caatctgcat gtcc                                          24

<210> SEQ ID NO 7
<211> LENGTH: 24
<212> TYPE: DNA
<213> ORGANISM: Artificial Sequence
<220> FEATURE:
<223> OTHER INFORMATION: primer for PCR genotyping

<400> SEQUENCE: 7
gccccgtcat gcattatctc cttg                                          24
```

```
<210> SEQ ID NO 8
<211> LENGTH: 24
<212> TYPE: DNA
<213> ORGANISM: Artificial Sequence
<220> FEATURE:
<223> OTHER INFORMATION: primer for PCR genotyping

<400> SEQUENCE: 8
cgctcagggc tacatacacc atgg                                          24

<210> SEQ ID NO 9
<211> LENGTH: 23
<212> TYPE: DNA
<213> ORGANISM: Artificial Sequence
<220> FEATURE:
<223> OTHER INFORMATION: primer for PCR genotyping

<400> SEQUENCE: 9
ctcatcgagt aacgcaggcg acg                                           23

<210> SEQ ID NO 10
<211> LENGTH: 24
<212> TYPE: DNA
<213> ORGANISM: Artificial Sequence
<220> FEATURE:
<223> OTHER INFORMATION: primer for PCR genotyping

<400> SEQUENCE: 10
catggatgga caagagattg cacg                                          24

<210> SEQ ID NO 11
<211> LENGTH: 24
<212> TYPE: DNA
<213> ORGANISM: Artificial Sequence
<220> FEATURE:
<223> OTHER INFORMATION: primer for PCR genotyping

<400> SEQUENCE: 11
ttcactgcta caattctgtc cagc                                          24

<210> SEQ ID NO 12
<211> LENGTH: 24
<212> TYPE: DNA
<213> ORGANISM: Artificial Sequence
<220> FEATURE:
<223> OTHER INFORMATION: primer for PCR genotyping

<400> SEQUENCE: 12
cagtccaaat caggcggtag caga                                          24

<210> SEQ ID NO 13
<211> LENGTH: 24
<212> TYPE: DNA
<213> ORGANISM: Artificial Sequence
<220> FEATURE:
<223> OTHER INFORMATION: primer for PCR genotyping

<400> SEQUENCE: 13
tgagaaggat cggaatcgag tggt                                          24

<210> SEQ ID NO 14
<211> LENGTH: 24
<212> TYPE: DNA
<213> ORGANISM: Artificial Sequence
<220> FEATURE:
<223> OTHER INFORMATION: primer for PCR genotyping
```

-continued

```
<400> SEQUENCE: 14
cttcgagctt cgtattccat cttc                                              24

<210> SEQ ID NO 15
<211> LENGTH: 24
<212> TYPE: DNA
<213> ORGANISM: Artificial Sequence
<220> FEATURE:
<223> OTHER INFORMATION: primer for PCR genotyping

<400> SEQUENCE: 15
ggtggttgtt atcaaagtcc tgct                                              24

<210> SEQ ID NO 16
<211> LENGTH: 24
<212> TYPE: DNA
<213> ORGANISM: Artificial Sequence
<220> FEATURE:
<223> OTHER INFORMATION: primer for PCR genotyping

<400> SEQUENCE: 16
atcatatcgc catcgccatc gtca                                              24

<210> SEQ ID NO 17
<211> LENGTH: 24
<212> TYPE: DNA
<213> ORGANISM: Artificial Sequence
<220> FEATURE:
<223> OTHER INFORMATION: primer for PCR genotyping

<400> SEQUENCE: 17
cgagaacact catgttggca tcga                                              24

<210> SEQ ID NO 18
<211> LENGTH: 24
<212> TYPE: DNA
<213> ORGANISM: Artificial Sequence
<220> FEATURE:
<223> OTHER INFORMATION: primer for PCR genotyping

<400> SEQUENCE: 18
aggacaatcg tccgcgaaag ttga                                              24

<210> SEQ ID NO 19
<211> LENGTH: 24
<212> TYPE: DNA
<213> ORGANISM: Artificial Sequence
<220> FEATURE:
<223> OTHER INFORMATION: primer for PCR genotyping

<400> SEQUENCE: 19
tcataaggga ttcaggcaag ggtg                                              24

<210> SEQ ID NO 20
<211> LENGTH: 24
<212> TYPE: DNA
<213> ORGANISM: Artificial Sequence
<220> FEATURE:
<223> OTHER INFORMATION: primer for PCR genotyping

<400> SEQUENCE: 20
tagcaccaga gtaggactca gata                                              24
```

<210> SEQ ID NO 21
<211> LENGTH: 24
<212> TYPE: DNA
<213> ORGANISM: Artificial Sequence
<220> FEATURE:
<223> OTHER INFORMATION: primer for PCR genotyping

<400> SEQUENCE: 21
agagctttgc cgtagaactt catg                                          24

<210> SEQ ID NO 22
<211> LENGTH: 24
<212> TYPE: DNA
<213> ORGANISM: Artificial Sequence
<220> FEATURE:
<223> OTHER INFORMATION: primer for PCR genotyping

<400> SEQUENCE: 22
ccccgacaat ctagcatacc ttcg                                          24

<210> SEQ ID NO 23
<211> LENGTH: 24
<212> TYPE: DNA
<213> ORGANISM: Artificial Sequence
<220> FEATURE:
<223> OTHER INFORMATION: primer for PCR genotyping

<400> SEQUENCE: 23
cggtgatgat gacaagcctt ggac                                          24

<210> SEQ ID NO 24
<211> LENGTH: 24
<212> TYPE: DNA
<213> ORGANISM: Artificial Sequence
<220> FEATURE:
<223> OTHER INFORMATION: primer for PCR genotyping

<400> SEQUENCE: 24
cagcctccca atcgcataaa tcgt                                          24

<210> SEQ ID NO 25
<211> LENGTH: 24
<212> TYPE: DNA
<213> ORGANISM: Artificial Sequence
<220> FEATURE:
<223> OTHER INFORMATION: primer for PCR genotyping

<400> SEQUENCE: 25
aactcatcta caaggcgtgc caga                                          24

<210> SEQ ID NO 26
<211> LENGTH: 24
<212> TYPE: DNA
<213> ORGANISM: Artificial Sequence
<220> FEATURE:
<223> OTHER INFORMATION: primer for PCR genotyping

<400> SEQUENCE: 26
tcgacgcttg cgagtcctgt gcct                                          24

<210> SEQ ID NO 27
<211> LENGTH: 24
<212> TYPE: DNA
<213> ORGANISM: Artificial Sequence
<220> FEATURE:
<223> OTHER INFORMATION: primer for PCR genotyping

```
<400> SEQUENCE: 27
aaacttgacg ccgaaccgct cctg                                              24
```

TALL FESCUE ENDOPHYTE ISOLATE 647

CROSS REFERENCE TO RELATED APPLICATIONS

This is the U.S. National Stage of International Application No. PCT/EP2013/067522, filed Aug. 23, 2013, which was published in English under PCT Article 21(2), which in turn claims the benefit of U.S. Provisional Application No. 61/692,810, filed Aug. 24, 2012.

FIELD

This disclosure relates to a new tall fescue grass endophyte referred to as 647. This new endophyte does not produce detectable ergovaline or any other ergopeptide alkaloids which are known to be harmful to grazing livestock. In addition, presence of the 647 endophyte can provide increased resistance to black beetles and thereby reduce damage to grass plants.

PARTIES TO JOINT RESEARCH AGREEMENT

DLF Trifolium A/S and the University of Aarhus Denmark are parties to a joint research agreement governing inventions disclosed herein.

BACKGROUND

Tall fescue (*Festuca arundinacea* Schreb.) is a cool season, perennial, sod forming bunch grass grown on over 35,000,000 acres (141,640 km$^2$) (Ball et al., 1993) of pasture and forage land in the United States, including 17 million acres (68,797 km$^2$) in Missouri (Roberts, C. A., 2000), 5.5 million acres (22,257 km$^2$) in Kentucky (Lacefield and Evans, 1984), 1 million acres (4,047 km$^2$) in each Georgia (Hancock, D., 2011), and Indiana (Cherney and Johnson, 1993). Tall fescue supplies most of the nutrients needed by more than 20 percent of United States beef cattle herds (West and Waller, 2007).

In 1931, Dr. Fergus of the University of Kentucky discovered a tall fescue ecotype while visiting the Suiter Farm in Menifee County, Kentucky. After 12 years of testing in Kentucky, the tall fescue cultivar was released as Kentucky 31 in 1943 (Lacefield and Evans, 1984). Most tall fescue, including Kentucky 31, in the United States is infected with a wild-type fungal endophyte, *Neotyphodium coenophialum* (former known as *Acremonium coenophialum*) that is toxic to animals, causing a syndrome known as fescue toxicosis or summer slump.

Fescue toxicosis is a disorder of all domestic grazing animals, including; cattle (*Bos* spp.), sheep (*ovis* spp.), and horses (*Equus* spp.) grazing endophyte (*Neotyphodium coenophialum*) infected tall fescue. Fescue toxicosis can cause decreased weight gain from 30 to 100% for grazing steers (Paterson et al., 1995), decreased milk production (Peters et al., 1992), decreased pregnancy rates (Schmidt et al., 1986), and increased respiration rate, and body temperature (Zanzalari et al., 1989). Fescue toxicosis is one of the most costly animal disorders facing the livestock industry in the eastern United States, affecting over 8.5 million cattle (Ball et al., 2007) and costing the United States beef industry an estimated $609 million annually in lost revenue because of reduced reproductive and growth rates in cattle herds (Hoveland, 1993).

To combat the effects of fescue toxicosis, the first *Acremonium coenophialum* free tall fescue variety, AU Triumph, was released in 1983. Animal performance was reported to be excellent (Hoveland et al., 1982), with annual forage production equal to or greater than Kentucky 31 (Pedersen et al, 1983). AU Triumph was however reported to be less tolerant to cold, drought, and overgrazing than Kentucky 31 E+ (where E+ means that the variety has a high content of endophyte), resulting in stand losses in overgrazed stressful environments.

Although the wild-type endophyte's toxins cause livestock disorders, infection of tall fescue cultivars with a *Neotyphodium* endophyte and the resulting host plant-endophyte interactions often results in improved tolerance to abiotic (Arachevaleta et al., 1988) and biotic (Popay and Bonos, 2008) stresses and improved overall persistence of cool-season perennial grasses.

One management strategy for minimizing the effects of tall fescue toxicosis is the replacement of toxic tall fescue with cultivars that are endophyte-free or contain non-toxic endophytes.

SUMMARY

Herein disclosed is an isolated *Neotyphodium coenophialum* endophyte (647) that can be used to inoculate tall fescue grass plants. In a particular example, the endophyte is present in an axenic culture of an endophyte deposited with The Centraalbureau voor Schimmelcultures (CBS) in The Netherlands, as Deposit No. CBS 133163 on Jul. 31, 2012, under the Budapest Treaty. This endophyte will be irrevocably and without restriction released to the public upon the issuance of a patent. Therefore, this endophyte is known and readily available to the public. In one example, the disclosure provides the 647 endophyte deposited as Deposit No. CBS 133163. This endophyte can be used to form symbiotic host relationships with grass plants and is different from all known endophytes.

It is shown herein that the 647 endophyte increases the fresh weight yield of tall fescues, such as the variety Martin 2, as compared to grass plants without the endophyte, such as an increase of at least 5%, at least 10%, or at least 15% measured on single plants in a pot trial. In addition, the 647 endophyte produces no detectable ergovaline (0 ppm) and was not toxic to grazing animals, in contrast to Kentucky 31 with its native endophyte, for example as evidenced by higher prolactin levels and increased weight gain when animals were allowed to graze on tall fescue inoculated with 647 endophyte. It is also shown herein that presence of the 647 endophyte can reduce damage due to black beetles (*Heteronychus arator*), for example as evidenced by a reduction in the number of severely damaged tillers, such as a reduction of at least 5%, at least 10%, at least 20%, at least 30%, at least 40%, at least 50%, or even at least 60%, in the presence of the 647 endophyte. Presence of the 647 endophyte can also increase the dry matter of live tillers, such as an increase of at least at least 5%, at least 10%, at least 20%, at least 30%, at least 40%, at least 50%, or even at least 60%, in the presence of the 647 endophyte.

The foregoing and other objects and features of the disclosure will become more apparent from the following detailed description, which proceeds with reference to the accompanying figures.

DETAILED DESCRIPTION

Provided herein is a *Neotyphodium coenophialum* endophyte referred to as 647. This endophyte was originally isolated from a wild tall fescue, and can be used to inoculate other grasses, such as other forage grasses, to provide the benefits associated with the presence of endophyte 647.

It is shown herein that the 647 endophyte increases the fresh weight yield of tall fescues, such as Martin 2, as compared to grass plants (such as a tall fescue) without the endophyte. In some examples, the 647 endophyte can increase the fresh weight yield of tall fescue or other forage grass, for example an increase of at least 5%, at least 10%, at least 11%, at least 12%, at least 13%, at least 14%, or at least 15% as compared to the fresh weight yield of the grass (such as a tall fescue) without the 647 endophyte.

The 647 endophyte was used in a grazing trial. Tall fescue cultivars were artificially inoculated with non-ergot alkaloid producing endophytes to evaluate differences between wild-type and non-toxic endophytes. Three Polypay yearling ewes were assigned to one of six different pasture treatments containing either non-ergovaline alkaloid producing endophytes (207, 647, or Gold™), ergovaline producing endophytes (Kentucky 31 E+), or no endophytes cultivars Martin 2 and AU Triumph (Reg. No. CV-21, PI 601106) in 0.1 hectare replicated pasture treatments. The 36 ewes were evaluated for changes in body weight, serum prolactin, and rectal temperatures during three grazing periods over three years (2009 to 2011) to determine animal performance and evaluate fescue toxicosis. The nutritional quality of endophyte-infected tall fescue was shown to be comparable to other tall fescues that did not contain the *Neotyphodium* endophyte. Ergovaline alkaloid concentration was only found in detectable amounts in the Kentucky E+ forage, when sampled during each year of the each grazing period. Pre-treatment sheep body weight did not differ (P<0.9948) among treatments. Mean total weight gain (kg) was lower (P=0.0039) for Kentucky 31 E+ compared to 207, 647, Gold™, and E−. Mean average daily gain was lower (P=0.0026) for Kentucky 31 E+ compared to 207, 647, Gold™, and E−. Pre-treatment serum prolactin concentration did not differ (P=0.5526) among treatments. Post-treatment prolactin level showed a highly significant effect in the 3 year mean (P<0.0001). Serum prolactin concentrations in sheep consuming wild-type endophyte fescue (Kentucky 31 E+) were lower than those sheep consuming endophyte fescues that did not produce the ergovaline alkaloid at detectable levels. No differences in rectal temperatures were observed, either; pre-treatment (P=0.8404), treatment (P=0.7180), or post-treatment (P=0.5905). The rectal temperature measurements were subjected to confounding variables, such as sheep handling stress, and ambient air temperature.

Thus, the data provided herein show that the 647 endophyte produces no detectable ergovaline and was non-toxic to grazing animals (such as sheep) in contrast to Kentucky 31 with its native endophyte, for example as evidenced by higher prolactin levels and increased weight gain when animals were allowed to graze on tall fescue inoculated with 647 endophyte. In some examples, animals allowed to graze on grasses containing the 647 endophyte have prolactin levels that are at least 1.5 fold, at least 2-fold, at least 3-fold, at least 4-fold, at least 5-fold, at least 6-fold, at least 7-fold, or at least 7.5-fold higher than animals allowed to graze on Kentucky 31 grass with its native endophyte. In some examples, animals allowed to graze on grasses containing the 647 endophyte weighed at least 1.5 fold, at least 2-fold, at least 2.5-fold, or at least 3-fold more than animals allowed to graze on Kentucky 31 grass with its native endophyte. Sheep grazing tall fescue cultivars inoculated with endophytes not producing ergovaline displayed total weight gains similar to sheep consuming cultivars not containing endophyte. Lowered prolactin concentration and depressed weight gain of sheep grazing Kentucky E+ tall fescue indicates that the use of non-toxic endophyte tall fescue cultivars is viable management strategy for minimizing the effects of tall fescue toxicosis in grazing animals such as sheep, cows, horses, and goats. Thus, the use of 647 provides a grass plant having reduced or undetectable amounts of the alkaloid ergovaline compared to naturally occurring endophyte/grass combinations, reduced toxicity to livestock compared to naturally occurring endophyte/grass combinations, or combinations thereof.

It is also shown herein that presence of the 647 endophyte provides increased resistance to black beetles, and thus can be used to reduce damage due the black beetles, for example as evidenced by a reduction in the number of severely damaged tillers. In some examples, grasses (such as a tall fescue) inoculated with 647 have fewer severely damaged tillers by black beetles or other insects (such as Argentinian stem weevil (*Listronotus bonariensis*), pasture mealy bug (*Balanococcus poae*) or other leaf eating insects), such as a reduction of at least 10%, at least 20%, at least 30%, at least 40%, at least 50%, or even at least 60%, as compared to the grass (such as a tall fescue) without the 647 endophyte. Thus, the 647 endophyte can be used to provide a grass plant increased resistance to black beetles or other insects, for example by reducing infestation by black beetles or other insect.

Data provided herein demonstrate that inoculation of grasses with the 647 endophyte can increase the dry matter of live tillers. In some examples, grasses (such as a tall fescue) inoculated with 647 have more dry matter of live tillers, such as an increase of at least 5%, at least 10%, at least 20%, at least 30%, at least 40%, at least 50%, or even at least 60%, as compared to the grass (such as a tall fescue) without the 647 endophyte.

In some examples, endophyte 647 can form a stable synthetic combination with a grass host, such as turf grass or forage grass. Exemplary forage grasses that can be inoculated with 647 include but are not limited to any tall fescue (*Festuca arundinacea*), such as cultivars Martin 2, Tower, or IS-FTF 68. In one example, the disclosure provides a stable synthetic combination of endophyte 647 and a grass host, such as a lawn or turf grass, or a forage grass. In a specific example the grass is a bentgrass (common or creeping), fescue (such as a tall, red, meadow or fine fescue), ryegrass (annual or perennial *Lolium* species), bromegrass, and the like.

A "synthetic endophyte/grass combination" is the combination of an endophyte and a grass cultivar (such as a tall fescue or other grass species) each of which has been isolated from nature, but the combination of which does not exist in nature. For example, the grass cultivar can be a culturally improved grass variety, such as having one or more desirable characteristics, such as improved grass yield and forage quality, increased persistence, drought tolerance, resistance to one or more diseases, and the like. Methods of making such a synthetic combination are known in the art (Johnson-Cicalese et al. 2000), and can include inoculating the desired grass cultivar (such as a tall fescue cultivar) with an axenic culture of endophyte 647, or crossing a synthetic endophyte/grass cultivar combination with an endophyte-free grass cultivar (such as a tall fescue cultivar) to form a new cultivar infected with the endophyte. In one example, the endophyte-free grass cultivar includes one or more desirable characteristics, such as improved yield and forage quality, disease resistance, herbicide resistance, drought resistance, salt resistance, persistence, low toxicity to grazing animals, and so forth.

Also provided by the present disclosure are seeds of the disclosed synthetic combinations. For example, such seeds can be harvested from grass plants (such as tall fescue or other grass plants) inoculated with the disclosed endophyte. In another example, the seeds are harvested from plants of the disclosed synthetic endophyte/grass combination grown from seeds harvested from grass plants inoculated with the endophyte.

Also provided is a method to screen for endophytes with properties similar to the endophyte 647. Example 3 illustrates the unique genetic background of the 647 isolate and allows the characterization of alternate isolates of *Neotyphodium coenophialum* endophyte with similar genetic and phenotypic character to the 647 isolate. Typically the method is a PCR based method using oligonucleotide primers adapted to amplify genetic microsatellite fragments as described in table 3.

The method comprises:
i) providing an isolated *Neotyphodium coenophialum* endophyte to be tested and extracting genomic DNA;
ii) forming a preparation comprising: one or more pairs of oligonucleotide probes adapted to anneal to genomic DNA comprising microsatellite nucleotide sequences selected from the group consisting of B1, B4, B9, B10, B11, NCESTA1AG05, NCESTA1DH04, NCESTA1FH03, NCESTA1IC04, NCESTA1GA07, NCESTA1AG12, NCESTA1FC04, and NCESTA1DB06; a thermostable DNA polymerase, deoxynucleotide triphosphates and co-factors;
iii) providing polymerase chain reaction conditions sufficient to amplify all or part of said genomic microsatellite DNA;
iv) analysing the amplified products of said polymerase chain reaction for the presence of genomic microsatellite DNA as defined in ii) above; and optionally v) comparing the amplified product with one or more *Neotyphodium coenophialum* endophytes including *Neotyphodium coenophialum* endophyte 647.

Provided are primer pairs suitable for use in the method according to the invention wherein the one or more primer pairs comprise nucleotide sequences selected from the group consisting of:
  i) SEQ ID NO: 1 and SEQ ID NO: 2 [B1];
  ii) SEQ ID NO: 3 and SEQ ID NO: 4 [B4];
  iii) SEQ ID NO: 5 and SEQ ID NO: 6 and SEQ ID NO: 7 [B9];
  iv) SEQ ID NO: 8 and SEQ ID NO: 9 [B10];
  v) SEQ ID NO: 10 and SEQ ID NO: 11 [B11];
  vi) SEQ ID NO: 12 and SEQ ID NO: 13 [NCESTA1DH04];
  vii) SEQ ID NO: 14 and SEQ ID NO: 15 [NCESTA1H03];
  viii) SEQ ID NO: 16 and SEQ ID NO: 17 [NCESTA1AG05];
  ix) SEQ ID NO: 18 and SEQ ID NO: 19 [NCESTA1IC04];
  x) SEQ ID NO: 20 and SEQ ID NO: 21 [NCESTA1GA07];
  xi) SEQ ID NO: 22 and SEQ ID NO: 23 [NCESTA1AG12];
  xii) SEQ ID NO: 24 and SEQ ID NO: 25 [NCESTA1FC04]; and
  xiii) SEQ ID NO: 26 and SEQ ID NO: 27 [NCESTA1DB06].

Provided are *Neotyphodium coenophialum* endophytes isolated by the screening method that has the following characteristics:
  i) the new endophyte does not produce detectable ergovaline or any other ergopeptide alkaloids which are known to be harmful to grazing livestock; and/or
  ii) the new endophyte has increased resistance to black beetles and thereby reduce damage to grass plants.

The following examples are provided to better describe the present disclosure and to guide those of ordinary skill in the art in the practice of the present disclosure. The singular forms "a," "an," and "the" refer to one or more than one, unless the context clearly dictates otherwise. For example, the term "comprising a grass plant" includes single or plural plants and is considered equivalent to the phrase "comprising at least one grass plant." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements.

Unless explained otherwise, all technical and scientific terms used herein have the same meaning as commonly understood to one of ordinary skill in the art to which this disclosure belongs. All references cited herein are incorporated by reference.

The foregoing and other objects and features of the disclosure will become more apparent from the following detailed description of several embodiments.

EXAMPLE 1

Endophyte Isolation and Inoculation of Tall Fescue

This example describes methods used to isolate the 647 endophyte from a wild-type fescue, and to inoculate the Martin 2 variety with the 647 endophyte.

The 647 endophyte was isolated from a tall fescue. Routine methods of endophyte isolation were used. Briefly, seeds were sterilized in a solution of 1.9% (v/v) sodium hypochlorite and 0.1% (v/v) Triton X-100 for 15 minutes, washed four times with distilled water, and incubated in water overnight to allow any viable microbial spores to germinate. The sodium hypochlorite treatment was repeated the following day and the seeds were rinsed four times with sterile water in a laminar flow cabinet and plated onto potato dextrose agar (PDA) plates. The plates were incubated under light, which allowed the germinating seedlings to continue to grow. After the seeds germinated it was sometimes necessary to aseptically push the seedling back into the agar surface using sterile forceps. The fungal endophytes emerged from the seedlings in about 2 weeks. Fungal cultures were maintained by subculturing every 2 to 3 weeks. To aid in removing mycelium from the plates, fungi were subcultured on PDA plates overlaid with a piece of cellophane.

The resulting isolated endophytes were used to inoculate shoots from mature Martin 2 variety plants using routine methods (Johnson-Cicalese et al. 2000). Briefly, Martin 2 endophyte-free status was confirmed by microscopic examination of leaf sheath tissue. Plants to be inoculated were separated into individual tillers with roots and washed in water to remove excess soil. The leaf blades were trimmed to about 3 cm. A vertical slit about 2 mm long was made at the junction between the root and shoot using a 16 gauge syringe needle. A small piece of 647 fungal mycelium was then removed from the culture plate using the tip of the needle and inserted into the slit. The tiller was then immediately planted into potting mix and returned to the greenhouse. New growth was microscopically examined for the presence of endophyte.

EXAMPLE 2

Tall Fescue Yield Trial

This example describes methods used to identify endophyte-containing fescues that have higher fresh weight yield than fescues without endophyte.

Materials and Methods

The 2005 forage tall fescue trial was sown on 10 Oct. 2005 near Berry, Ky. (38.538667-84.3925) on Ashton silt loam with a 0 to 2 percent slope. The land area produced an annual tobacco crop the previous year and a winter wheat crop that was harvested prior to being tilled in preparation for this trial. The average annual monthly maximum temperature was 19° C. and 21° C. during 2005 and 2006, respectively. The site received 914 mm and 1,142 mm of precipitation in 2005 and 2006, respectively.

The trial consisted of 16 entries arranged in a complete randomized block design with two replications Each plot was originally drilled at 8.4 m² consisted of seven rows drilled on 23.3 cm centers with a Hege 1000 cone plot drill with 30.5 cm between plots at a seeding rate of 29.43 kg per hectare at a depth of 12.7 mm. The plot ends were sprayed to a consistent length following establishment in the fall of 2005 and measured following the first harvest in the spring of 2006 with a finished plots size of averaging 7.7 m².

The trial area received 56 kg per hectare of actual nitrogen as 19-19-19 (NPK) prior to sowing in 2005 and again in the fall of 2006. Nitrogen was also applied in the spring of 2006 and 2007 prior to the first harvest at a rate of 56 kg per hectare of actual nitrogen as Ammonium nitrate and again following each harvest.

In the spring of 2006 and 2007, the trial area received one broadcast application of Prowl®3.3 EC herbicide (37.4% Pendimethalin) at a rate 0.91 liters per hectare (4.8 pints/A) in 95 liters of water and one application of 2,4-D Amine broadleaf herbicide (46.3% Dimethylamine salt of 2,4-D-Dichlorophenoxyacetic acid) at a rate of 0.57 liters per hectare (3.0 pints/A) in 95 liters of water.

The trial was harvested four times in 2006 and two times in 2007. Fresh weight yield was collected on all harvest. During each harvest (Table 1) the trial was cut with a Haldrup plot harvester at a plot height 5 cm.

TABLE 1

| | Harvest dates | |
|---|---|---|
| | 2006 | 2007 |
| 1 | 15 May | 8 May |
| 2 | 22 June | 9 July |

TABLE 1-continued

| | Harvest dates | |
|---|---|---|
| | 2006 | 2007 |
| 3 | 23 August | |
| 4 | 10 November | |

Results

As shown in Table 2, Martin 2 with endophyte 647 showed significantly higher fresh weight yield than Martin 2 without endophyte. Thus, endophyte 647 was selected for further analysis.

TABLE 2

Fresh weight yield of tall fescues

| Name | 2006-07 total fresh weight yield, kg/ha |
|---|---|
| Martin 2 | 68495 |
| Martin 2 + 647 | 79218 |
| Duramax | 75141 |
| Duramax + GOLD | 80038 |
| Kentucky 31 + wild type endophyte | 83559 |
| LSD (0.05) | 10329 |

EXAMPLE 3

Genetic Marker Characterization of Endophyte Isolate 647

This example describes methods used to genetically characterize endophyte 647.

Isolation of Genomic DNA

Genomic DNA was isolated from endophyte infected plant tillers. Three or four tillers from each plant were harvested, and wilted leaf tissue was removed. The basal 2 to 3 cm of tiller material were crushed in a leaf press (MERKU, Germany). The resulting plant sap was dissolved in 400 µL extraction buffer (200 mM Tris HCl pH 7.5, 250 mM NaCl, 25 mM NaEDTA, 1% SDS) and incubated for 15 min at room temperature. Then 400 µL 5 M potassium acetate were added and the samples were vortexed and incubated on ice for 30 min. The samples were centrifuged for 10 min (13000 rpm). 600 µL of each sample were transferred to a 1.5-mL centrifuge tube, and DNA was precipitated by adding 600 µL ice-cold isopropanol. The samples were vortexed and incubated on ice for 30 min followed by centrifugation for 10 min at 13,000 rpm. DNA pellets were washed in 300 µL 70% ethanol. The air-dried pellets were re-suspended in 1.25 mL distilled water.

Microsatellite Primers and Polymerase Chain Reaction (PCR) Amplification

A total of 13 endophyte microsatellite loci were examined. The microsatellites were B1, B4, B9, B10, B11 published by Moon et al. (1999) and NCESTA1AG05, NCESTA1DH04, NCESTA1FH03, NCESTA1IC04, NCESTA1GA07, NCESTA1AG12, NCESTA1FC04, and NCESTA1DB06 published by van Zijll de Jong et al. (2003). Polymerase chain reaction (PCR) amplifications were performed in 25-µL volumes according to Moon et al. (1999) with the exception that the primers were fluorescently labeled with IRD-800 (LI-COR, Lincoln, Nebr.). Reference strains from *F. arundinacea* included *N. coenophialum* isolate Tf27 and e19 (=ATCC 90664) both belonging to taxonomic group FaTG1, Tf13 and Tf15 (both taxonomic group FaTG-2), and Tf18 (FaTG-3). (Schardl et al., 1991; Christensen et al., 1993; Moon et al., 1999). All microsatellites were also tested on non-infected *F. arundinacea* DNA.

Electrophoresis of Microsatellite Markers

Gel electrophoresis and pattern visualization were performed using a LI-COR model 4000 automated fluorescent DNA sequencer (Middendorf et al., 1992) (LI-COR, Lincoln, Nebr.). Gel dimensions were 25 cm long and 0.25 mm thick. The gel contained 7 M urea and 7.0% SequaGel XR concentrate (National Diagnostics, Atlanta, Ga.). The running buffer was 0.4×TBE (dilution of 10×TBE: 0.9 M Tris, 0.9 M boric acid, 0.2 M EDTA). The gel was run at 2000 V constant voltage, and the gel temperature was maintained at 50° C. A 64 well comb was used for lane formation, and 0.6 μL of each sample was loaded. A size ladder was produced by mixing PCR products originating from amplifications of a known DNA sequence of *L. perenne*. The size ladder included 42, 44, 125, 126, 150, 151, 193, 251, 280, 327, 328, 414, and 551 base pair fragments and was loaded in lanes 1, 32, and 64. In addition, a positive control of an endophyte isolated from a DLF-Trifolium *F. arundinacea* breeding line was run on each gel as an internal standard.

Results

The observed marker sizes of endophyte 647, as compared to reference samples and to endophytes on the market and described in other patent applications, are shown in Tables 3-5.

TABLE 3

Observed marker sizes of endophyte 647 compared to reference samples:

| Name | Taxonomic group | B11 | B10 | B1 | B4 | B9 |
|---|---|---|---|---|---|---|
| 647 | | 128/194 | 160/180/185 | 300 | 102 | 181/184 |
| TF_27 | FaTG1 | 150/196 | 167/176/191 | 300 | 102/106/108 | 181/184 |
| E_19 | FaTG1 | 150/196 | 167/176/191 | | 102/106/108 | 184 |
| TF_13 | FaTG2 | 128/142 | 176/191 | 300 | 102 | 184/187 |
| TF_15 | FaTG2 | 128/166 | 176/181 | 300 | 102 | 158/189 |
| TF_18 | FaTG3 | 128 | 186 | 235 | 123 | 184 |
| E34 Barenbrug | | 150/192 | 166/176/185 | 300 | 102/106 | 180/184 |
| MaxP AgResearch | | 182/194 | 166/176 | 300 | 102/106 | 180/184 |
| MaxQ AgResearch | | 182/194 | 166/176 | 300 | 102/106 | 180/184 |
| Gold Univeristy of Arkansas | | 166/196 | 166/176/188 | 300 | 102/106 | 180/184 |

TABLE 4

Observed marker sizes of endophyte 647 compared to reference samples:

| Name | Taxonomic group | NCESTA1AG05 | NCESTA1FH03 | NCESTA1GA07 | NCESTA1DH04 | NCESTA1FC04 |
|---|---|---|---|---|---|---|
| 647 | | 180/182 | 244/256 | 187 | 220/233 | 310 |
| TF_27 | FaTG1 | 180/182 | 244/252 | 187 | 220/225/230 | 310 |
| E_19 | FaTG1 | 180/182 | 244/252 | 187 | 220/225/230 | 310 |
| TF_13 | FaTG2 | 184/186 | 234/246 | 180/197 | 227/230 | 310 |
| TF_15 | FaTG2 | 192/194 | 238 | 180/193 | 220/230 | 310 |
| TF_18 | FaTG3 | 197 | 238 | 190 | 233/237 | 310 |
| E34 Barenbrug | | 180/182 | 244/250 | 187 | 216/222/228 | 310 |
| MaxP AgResearch | | 180/182 | 244/250 | 187 | 216/222/234 | 310 |
| MaxQ AgResearch | | 180/182 | 244/250 | 187 | 216/222/234 | 310 |
| Gold Univeristy of Arkansas | | 180/182 | 244/250 | 187 | 213/222/236 | 310 |

TABLE 5

Observed marker sizes of endophyte 647 compared to reference samples:

| Name | Taxonomic group | NCESTA1AG05 | NCESTA1FH03 | NCESTA1GA07 | NCESTA1DH04 | NCESTA1FC04 |
|---|---|---|---|---|---|---|
| 647 | | 180/182 | 244/256 | 187 | 220/233 | 310 |
| TF_27 | FaTG1 | 180/182 | 244/252 | 187 | 220/225/230 | 310 |
| E_19 | FaTG1 | 180/182 | 244/252 | 187 | 220/225/230 | 310 |
| TF_13 | FaTG2 | 184/186 | 234/246 | 180/197 | 227/230 | 310 |
| TF_15 | FaTG2 | 192/194 | 238 | 180/193 | 220/230 | 310 |
| TF_18 | FaTG3 | 197 | 238 | 190 | 233/237 | 310 |
| E34 Barenbrug | | 180/182 | 244/250 | 187 | 216/222/228 | 310 |
| MaxP AgResearch | | 180/182 | 244/250 | 187 | 216/222/234 | 310 |
| MaxQ AgResearch | | 180/182 | 244/250 | 187 | 216/222/234 | 310 |

TABLE 5-continued

Observed marker sizes of endophyte 647 compared to reference samples:

| Name | Taxonomic group | NCESTA1AG05 | NCESTA1FH03 | NCESTA1GA07 | NCESTA1DH04 | NCESTA1FC04 |
|---|---|---|---|---|---|---|
| Gold Univeristy of Arkansas | | 180/182 | 244/250 | 187 | 213/222/ 236 | 310 |

Thus, the observed marker sizes of endophyte 647 differ clearly from other known endophytes including those described in other patent applications, and thus endophyte 647 is unique.

EXAMPLE 4

Performance of Sheep Grazing Tall Fescue Cultivars Containing Non-Ergot Alkaloid Producing Endophytes This example describes methods used to determine the growth performance and toxicosis effects in sheep grazing tall fescue cultivars containing endophytes (207, 647, and Gold™ (Arkansas Strain 9)) which showed low levels of ergovaline production (Table 12), the ergopeptide primarily responsible for fescue toxicosis (Lyons et al., 1986). The protocol used was adapted from Parish et al. (2003).

Materials and Methods

Pasture Establishment

Six pasture treatments were established on Sep. 28, 2008 with the following tall fescue cultivars: Martin 2 inoculated with the endophyte designated 207, Martin 2 inoculated with the endophyte designated 647, Duramax inoculated with the endophyte Gold™ (Arkansas Strain 9), Kentucky 31 tall fescue containing the wild-type endophyte, AU Triumph endophyte free, and Martin 2 endophyte free. The experiment was developed with a randomized complete block design with two blocks for each pasture treatment. Each 0.1 hectare paddock was established near Corvallis, Oreg. Seed was drilled on 20 cm row centers into Bashaw clay soils with 3 to 12 percent slopes at a seeding rate of 27 kg per hectare. The paddocks were fertilized with 49 kg of nitrogen per hectare at establishment and prior to each grazing period in the early spring.

Grazing Management

Three Polypay yearling ewes were randomly assigned based on body weight to each pasture treatment at the start of each grazing period (Table 6). The entire treatment area was perimeter fenced with galvanized iron wire mesh field fence and cross fenced with 0.9 m tall ElectorNet electric netting (Premier Sheep Supplies, Washington, Iowa 52353).

TABLE 6

Grazing period dates

| Season | Dates | Duration (days) |
|---|---|---|
| Spring | Jun. 3 to Jul. 22, 2009 | 49 |
| | May 12 to Jul. 15, 2010 | 64 |
| | May 31 to Jun. 30, 2011 | 30 |

The ewes were allowed access to fresh water and free choice mineral (Wilbur-Ellis, Clackamas, Oreg. 97015) (Table 7) in each paddock. Ewes were shorn, ear-tagged, paint branded, docked, and treated for internal parasites with Ivomec Sheep Drench (0.08% Ivermectin) (Merial Limited, Duluth, Ga. 30096) at a rate of 0.2 mg/kg of body weight at the beginning of each grazing period.

TABLE 7

Composition of free choice mineral supplement

| | | Guaranteed Analysis |
|---|---|---|
| Calcium | (min) | 8.30% |
| Calcium | (max) | 9.30% |
| Phosphorus | (min) | 6.00% |
| Magnesium | (min) | 2.70% |
| Salt | (min) | 35.10% |
| Salt | (max) | 38.90% |
| Cobalt | (min) | 60 ppm |
| Iodine | (min) | 210 ppm |
| Manganese | (min) | 1700 ppm |
| Selenium | (min) | 200 ppm |
| Zinc | (min) | 7700 ppm |
| Vitamin A | (min) | 116120 IU/kg |
| vitamin D | (min) | 14515 IU/kg |
| Vitamin E | (min) | 23 IU/kg |

Feed 14.17 g per head per day
Manufactured by: Wilbur-Elli Company, Clackamas, Oregon 97015

Data Collection

Sheep body weights, blood samples, and rectal temperatures were collected at the beginning of each grazing period and at approximately two week intervals for the duration of the grazing period. During 2009, on dates the sheep were weighted, the ewes were gathered at approximately 10:00 AM from all pasture treatments, transported 0.4 km to the working facilities for data collection in a random order before being returned to the paddocks and sorted into the pasture treatments within approximately two hours. After 2009, on dates the sheep were weighted, the ewes were gathered at approximately 09:00 AM from their pasture treatment for data collection and returned to their pasture treatment within approximately 20 minutes. Approximately 10 ml blood samples were collected via jugular venipuncture, split into equal size sampled, centrifuged (to separate and harvest serum) and frozen (0° C.). The harvested serum was sent for prolactin radioimmunoassay. Weights were measured using a lamb balance scales (Arkfeld Manufacturing and Distributing Co., Norfork, Nebr. 68701).

At the beginning of the grazing period, pasture treatments were sampled for forage by clipping herbage to approximately a 5 cm stubble height in 10 random locations within each pasture. The random samples were pooled to make a composite sample that was separated into two separate equal size samples, which were air dried. One sample was used to determine the total ergot alkaloid concentrations, which were sent to one endophyte testing laboratory during 2009 (Oregon State University Endophyte Testing Laboratory) and to another laboratory during 2010 and 2011 (University of Missouri Veterinary Medical Diagnostic Laboratory) for analysis. The remaining sample was sent for chemical forage quality analysis (Dairyland Laboratories, Arcadia, Wis. 54612), during each year.

In the fall of 2009, approximately 50 tall fescue vegetative tillers were collected from each pasture treatment. The vegetative tillers were cut from the remaining plant just below the soil surface. Roots and leaf blades were removed from the tillers and the tiller section was cut 2.5 to 5.0 cm to determine the percent endophyte infection of each pasture treatment using the tissue print-immunoblot method described by Gwinn et al., 1991.

Statistical Analysis

Data was analyzed with general linear model regression (PROC GLM) with the appropriate error terms to test relationships between treatment and methods of analysis (SAS Institute). Mean separation was determined by one-way Students t-test means separation at p=0.05.

Results and Discussion

Forage Quality

The nutritional quality of endophyte-infected tall fescue was shown to be comparable to other tall fescues that did not contain the *Neotyphodium* endophyte (Table 8). Acid detergent fiber (P=0.0874), neutral detergent fiber (P=0.1473) and crude protein (P=0.1668) as a percent of dry matter (DM) showed no significant difference between the endophyte infected (E+) and endophyte free (E−) cultivars in the three year mean.

TABLE 8

Forage quality

| Cultivar | Parameter | Spring 2009 | Spring 2010 | Spring 2011 | 3 Year Mean |
|---|---|---|---|---|---|
| Martin 2 | ADF, % of DM | $29.93^b$ | $35.32^{abc}$ | $43.42^a$ | $36.27^a$ |
| | NDF, % of DM | 52.74 | 59.19 | 68.43 | $60.07^a$ |
| | CP, % of DM | 6.41 | 14.79 | $7.17^c$ | $9.45^{ab}$ |
| Martin 2 207 | ADF, % of DM | $31.44^{ab}$ | $34.08^c$ | $37.44^b$ | $34.32^b$ |
| | NDF, % of DM | 53.92 | 55.74 | 61.64 | $57.10^{ab}$ |
| | CP, % of DM | 6.54 | 17.02 | $9.28^{ab}$ | $10.95^a$ |
| Martin 2 647 | ADF, % of DM | $32.24^{ab}$ | $36.91^a$ | $40.15^{ab}$ | $36.43^b$ |
| | NDF, % of DM | 54.36 | 62.17 | 65.23 | $60.58^a$ |
| | CP, % of DM | 6.42 | 13.92 | $8.32^{abc}$ | $9.55^{ab}$ |
| Au Triumph | ADF, % of DM | $32.62^a$ | $34.79^{bc}$ | $39.70^{ab}$ | $35.70^{ab}$ |
| | NDF, % of DM | 54.60 | 59.12 | 63.51 | $59.07^{ab}$ |
| | CP, % of DM | 6.77 | 14.42 | $9.76^a$ | $10.31^{ab}$ |
| Duramax Gold | ADF, % of DM | $31.83^{ab}$ | $36.12^{ab}$ | $39.72^{ab}$ | $35.88^{ab}$ |
| | NDF, % of DM | 52.93 | 60.56 | 64.00 | $59.16^{ab}$ |
| | CP, % of DM | 6.02 | 13.64 | $7.95^{bc}$ | $9.20^b$ |
| Kentucky 31 E+ | ADF, % of DM | $31.29^{ab}$ | $35.78^{abc}$ | $37.48^b$ | $34.85^{ab}$ |
| | NDF, % of DM | 52.98 | 54.11 | 60.35 | $55.81^b$ |
| | CP, % of DM | 5.89 | 16.98 | $9.67^{ab}$ | $10.84^{ab}$ |

Means with different superscripts differ, p < 0.05.
Means lacking superscripts are not declared significant, p < 0.05
CP (%) = Crude Protein.
ADF (%) = Acid detergent fiber.
NDF (%) = Neutral detergent fiber.

Weight Gain

Mean pre-treatment body weights did not differ significantly (P=0.9948) between treatment groups (Table 9). Mean total weight gain was lower (P=0.0039) for Kentucky 31 E+ than all other treatments (Table 10). Average daily gain was higher (P=0.0026) for ewes grazing 207, 647, Gold™, and endophyte free cultivars compared to Kentucky 31 E+ (Table 11). No significant difference (P=0.0039) in three year total weight gain was observed between the non-endophyte cultivars (Martin 2 and Au Triumph) and the cultivars containing non-ergot alkaloid producing endophytes (207, 647, and Gold™) (Table 10), indicating no negative effect on weight gain as seen with Kentucky 31 E+ containing the wild-type endophyte.

TABLE 9

Mean pre-treatment (Day-0) weight, kg

| | Year | | | |
|---|---|---|---|---|
| Cultivar | Spring 2009+ (P = 0.9594) | Spring 2010‡ (P = 0.7212) | Spring 2011‡‡ (P = 0.6666) | Mean (P = 0.9948) |
| Martin 2 | 33.42 | 51.02 | 53.38 | 45.94 |
| Martin 2 207 | 34.55 | 49.52 | 53.52 | 45.86 |
| Martin 2 647 | 33.73 | 47.78 | 56.87 | 46.11 |
| Au Triumph | 34.18 | 47.78 | 55.72 | 45.89 |
| Duramax Gold ™ | 33.48 | 47.62 | 55.10 | 45.41 |
| Kentucky 31 E+ | 34.63 | 49.68 | 54.03 | 46.11 |

+Treatment day 0, Jun. 1, 2009.
‡Treatment day 0, May 12, 2010.
‡‡Treatment day 0, May 31, 2011
Means with different superscripts differ, p < 0.05.
Means lacking superscripts are not declared significant, p < 0.05

TABLE 10

Mean treatment weight gain, kg

| | Year | | | |
|---|---|---|---|---|
| Cultivar | Spring 2009+ (P < 0.0184) | Spring 2010‡ (P < 0.0005) | Spring 2011‡‡ (P < 0.0781) | Mean (P < 0.0039) |
| Martin 2 | $5.44^a$ | $3.55^b$ | $4.23^a$ | $4.41^{ab}$ |
| Martin 2 207 | $0.45^b$ | $8.32^a$ | $2.19^{ab}$ | $3.65^{ab}$ |
| Martin 2 647 | $2.27^b$ | $7.79^a$ | $4.08^{ab}$ | $4.71^a$ |
| Au Triumph | $0.23^b$ | $8.62^a$ | $1.51^b$ | $3.45^{ab}$ |
| Duramax Gold ™ | $1.59^b$ | $5.52^b$ | $2.35^{ab}$ | $3.15^b$ |
| Kentucky 31 E+ | $-0.30^b$ | $3.86^b$ | $1.21^b$ | $1.59^c$ |

+Treatment day 23 thru 51.
‡Treatment day 22 thru 64.
‡‡Treatment day 14 thru 30
Means with different superscripts differ, p < 0.05.
Means lacking superscripts are not declared significant, p < 0.05

TABLE 11

Average daily gain, g

| | Year | | | |
|---|---|---|---|---|
| Cultivar | Spring 2009+ (P < 0.0182) | Spring 2010‡ (P < 0.0009) | Spring 2011‡‡ (P < 0.0797) | Mean (P < 0.0026) |
| Martin 2 | $0.110^a$ | $0.057^b$ | $0.143^a$ | $0.103^a$ |
| Martin 2 207 | $0.010^b$ | $0.130^a$ | $0.075^{ab}$ | $0.072^{bc}$ |
| Martin 2 647 | $0.045^b$ | $0.122^a$ | $0.138^a$ | $0.102^{ab}$ |
| Au Triumph | $0.003^b$ | $0.135^a$ | $0.053^b$ | $0.064^c$ |
| Duramax Gold ™ | $0.033^b$ | $0.087^b$ | $0.078^{ab}$ | $0.066^c$ |
| Kentucky 31 E+ | $-0.007^b$ | $0.062^b$ | $0.042^b$ | $0.032^d$ |

+Day 51 of treatment.
‡Day 64 of treatment.
‡‡Day 30 of treatment
Means with different superscripts differ, p < 0.05.
Means lacking superscripts are not declared significant, p < 0.05

Endophyte Infection

The endophytes 207, 647, Gold™, and the wild-type endophyte in Kentucky 31 E+ had infection rates of 100, 96, 80 and 96 percent, respectively, at the time of sowing. The pasture treatment infection rate during late fall 2009 was 80, 90, 90, and 100 percent for 207, 647, Gold™, and the wild-type endophyte, respectively. Endophyte infection rate was determined in the seed by direct microscope technique (Latch et al., 1987) and in the tiller by tissue print-immunoblot (Gwinn et al., 1991).

Ergot Alkaloids

Ergovaline is the most abundant alkaloid of the ergopeptide alkaloids (Lyon et al., 1986), and the main alkaloid which causes fescue toxicosis. Ergovaline concentration was evaluated during each grazing period from air-dried forage samples. Mean ergovaline alkaloid concentration was only found in detectable amounts in the Kentucky 31 E+ (Table 12).

TABLE 12

Ergovaline concentration of air-dry forage sample, ppm

| Cultivar | Year | | | |
|---|---|---|---|---|
| | Spring 2009 (P = 0.0001) | Spring 2010 (P = 0.1225) | Spring 2011 (P = 0.1428) | Mean (P = 0.0001) |
| Martin 2 | $0.0^b$ | $0.0^b$ | $0.0^b$ | $0.0^b$ |
| Martin 2 207 | $0.0^b$ | $0.0^b$ | $0.0^b$ | $0.0^b$ |
| Martin 2 647 | $0.0^b$ | $0.0^b$ | $0.0^b$ | $0.0^b$ |
| Au Triumph | $0.0^b$ | $0.0^b$ | $0.0^b$ | $0.0^b$ |
| Duramax Gold ™ | $0.0^b$ | $0.0^b$ | $0.0^b$ | $0.0^b$ |
| Kentucky 31 E+ | $197.0^a$ | $117.5^a$ | $102.5^a$ | $139.0^a$ |

Means with different superscripts differ, $p < 0.05$.
Means lacking superscripts are not declared significant, $p < 0.05$.

Serum Prolactin

Figure 1A:
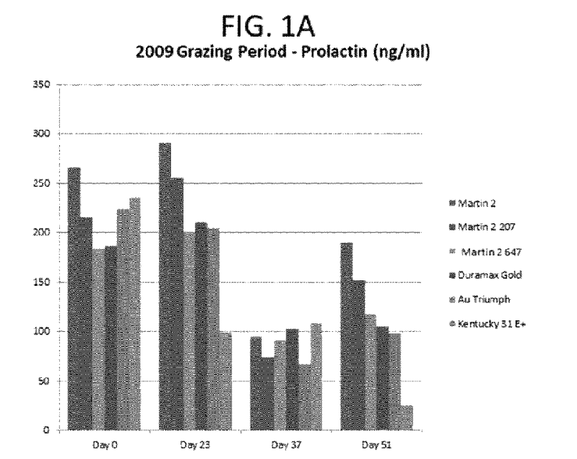
FIGS. 1A-1C are bar graphs showing the average grazing period prolactin level (ng/ml) of sheep grazing tall fescue treatments in (A) 2009, (B) 2010, and (C) 2011.
Figure 1B:
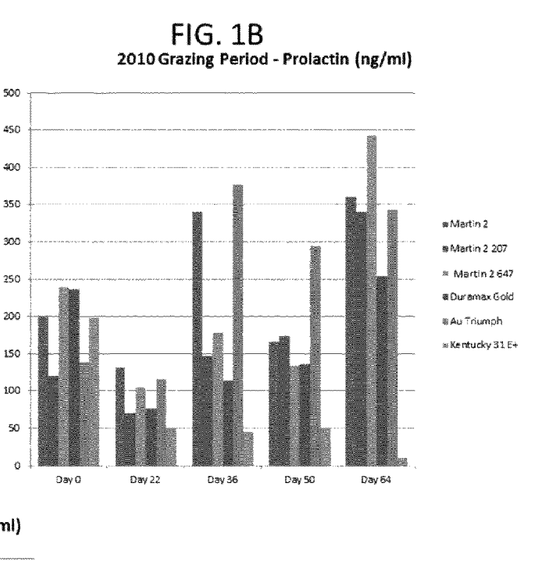
Figure 1C:
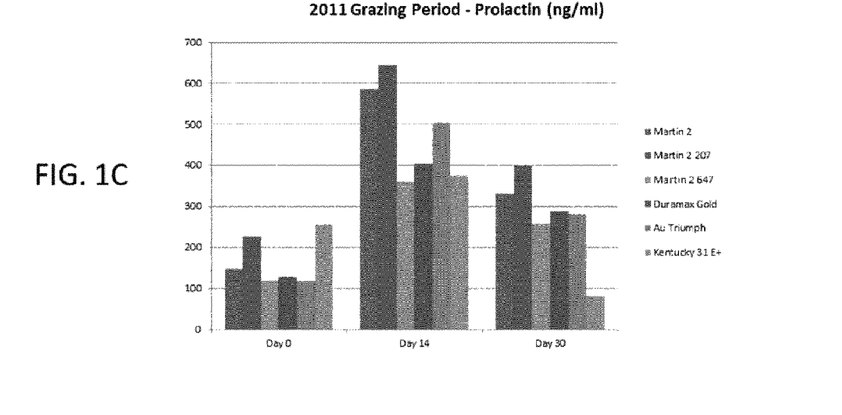

Lowered prolactin (PRL) concentrations (ng/ml) are known to be an indication of fescue toxicosis (Schillo et al., 1988). Mean pre-treatment (Day=0) prolactin levels did not differ (P=0.5526) among treatments in the three year mean (Table 13). Serum prolactin showed a decline as consumption of the toxic *Neotyphodium* endophyte continued over time (FIGS. 1A-1C, Table 14). Post-treatment prolactin level showed a highly significant effect in the 3 year mean (P=0.0001) (Table 15). Serum prolactin concentrations in sheep consuming wild-type endophyte fescue were lower than those sheep consuming endophyte fescues that did not produce the ergovaline alkaloid at detectable levels, in agreement with the results of Aldrich et al., 1993.

TABLE 13

Mean pre-treatment (Day-0) serum prolactin (PRL) concentrations, ng/ml

| Cultivar | Year | | | |
|---|---|---|---|---|
| | Spring 2009[+] (P = 0.5901) | Spring 2010[‡] (P = 0.5047) | Spring 2011[‡‡] (P = 0.1886) | 3 Year Mean (P = 0.5526) |
| Martin 2 | 265.90 | 199.98 | 146.80 | 168.50 |
| Martin 2 207 | 215.95 | 119.47 | 227.52 | 125.01 |
| Martin 2 647 | 183.44 | 239.27 | 120.07 | 154.12 |
| Au Triumph | 223.98 | 138.87 | 117.83 | 134.18 |
| Duramax Gold ™ | 186.02 | 236.40 | 128.87 | 153.97 |
| Kentucky 31 E+ | 234.98 | 198.03 | 257.35 | 157.54 |

[+]Treatment day 0, Jun. 1, 2009.
[‡]Treatment day 0, May 12, 2010.
[‡‡]Treatment day 0, May 31, 2011
Means with different superscripts differ, $p < 0.05$.
Means lacking superscripts are not declared significant, $p < 0.05$

TABLE 14

Mean treatment serum prolactin (PRL) concentrations, ng/ml

| Cultivar | Year | | | |
|---|---|---|---|---|
| | Spring 2009[+] (P = 0.0086) | Spring 2010[‡] (P = 0.0275) | Spring 2011[‡‡] (P = 0.2402) | 3 Year Mean (P = 0.0028) |
| Martin 2 | $191.70^a$ | $249.53^{ab}$ | 459.99 | $300.41^a$ |
| Martin 2 207 | $160.65^{ab}$ | $182.99^{ab}$ | 522.38 | $288.67^{ab}$ |
| Martin 2 647 | $136.53^b$ | $215.14^{ab}$ | 310.58 | $220.75^{ab}$ |
| Au Triumph | $123.28^{bc}$ | $282.70^a$ | 393.63 | $266.54^{ab}$ |
| Duramax Gold ™ | $139.47^b$ | $144.84^{bc}$ | 346.53 | $210.28^b$ |
| Kentucky 31 E+ | $77.58^c$ | $38.55^c$ | 228.58 | $114.90^c$ |

[+]Treatment day 23 thru 51.
[‡]Treatment day 22 thru 64.
[‡‡]Treatment day 14 thru 30
Means with different superscripts differ, $p < 0.05$.
Means lacking superscripts are not declared significant, $p < 0.05$

TABLE 15

Mean post-treatment serum prolactin (PRL) concentrations, ng/ml

| Cultivar | Year | | | |
|---|---|---|---|---|
| | Spring 2009[+] (P = 0.0550) | Spring 2010[‡] (P = 0.0562) | Spring 2011[‡‡] (P = 0.0343) | 3 Year Mean (P = 0.0001) |
| Martin 2 | $190.16^a$ | $360.87^a$ | $332.05^a$ | $294.36^a$ |
| Martin 2 207 | $152.12^{ab}$ | $340.70^a$ | $400.52^a$ | $297.78^a$ |
| Martin 2 647 | $117.78^{ab}$ | $442.72^a$ | $259.12^a$ | $273.20^a$ |
| Au Triumph | $97.55^{bc}$ | $343.12^a$ | $282.47^a$ | $241.04^a$ |
| Duramax Gold ™ | $105.37^{bc}$ | $253.03^a$ | $289.27^a$ | $215.89^a$ |
| Kentucky 31 E+ | $25.83^c$ | $10.17^b$ | $80.92^b$ | $38.97^b$ |

[+]Day 51 of treatment.
[‡]Day 64 of treatment.
[‡‡]Day 30 of treatment
Means with different superscripts differ, $p < 0.05$.
Means lacking superscripts are not declared significant, $p < 0.05$ The results from ergovaline and the prolactin demonstrate that the endophytes 207, 647, and Gold™ do not produce detectable levels of ergovaline or any other ergopeptide alkaloids which are harmful to the grazing sheep. This is confirmed by the total weight gain that is not significantly different from the endophyte free control cultivars (Martin 2 and Au Triumph), in contradiction to what was seen for Kentucky 31+, containing wild-type endophyte. The results clearly show that the endophytes 207, 647, and Gold™ are safe to use for grazing sheep or other livestock and is a viable management strategy for minimizing the effects of fescue toxicosis.

EXAMPLE 5

Evaluation of Endophyte-Infected Fescue Grasses for Protection Against Adult Black Beetles This example describes a replicated pot trial to evaluate endophyte-infected fescue lines for effects on black beetle adult feeding. There were 12 fescue lines which were run as two separate trials. Each trial included 5 endophyte-free lines as controls. Black beetle can cause serious damage to North Island pastures of New Zealand. Chemicals which once gave good control of black beetle have been banned from use, leaving few control measures available to farmers.

One plant from each fescue line was caged together in a ring so that beetles had a choice of plants to feed on. After 3 weeks containment, each plant was assessed for their number of live tillers, dead tillers, dry matter and the number of beetles found associated with each plant.

Materials and Methods

Tall fescue seed was used, including five endophyte-free lines as controls (Table 16).

TABLE 16

Tall fescue seed line and endophyte status

| Cultivar name | Endophyte name | Endophyte status |
|---|---|---|
| Martin2 | 647 | E+ |
| Martin2 | — | E− |
| Kentucky 31 | Wild-type | E+ |
| Tower | 647 | E+ |
| Tower | — | E− |

Trial Establishment

On Mar. 30, 2011, 50 seeds from each of the seed lines were placed on moistened filter paper in individual Petri dishes. After 7 days, 20 germinated seeds from each line were transferred into polystyrene trays containing potting mix and kept in a glasshouse where the seedlings were watered and trimmed when required. Black beetle adults were collected from March through to June from ryegrass pastures and fed on a carrot until required for the trial.

From the 30th June, all plants with at least 3 tillers were tested for endophyte using the tissue print immunoblot method (Hahn et al., 2003). Remaining plants with too few tillers and those with unclear results from the immunoblot method were tested by staining with analine blue followed by microscopic examination.

On August 4, 10 plants with the appropriate endophyte status from each fescue treatment were transplanted into individual planter bags (64 mm×64 mm×150 mm) containing potting mix. The number of tillers on each plant was counted then the plant was trimmed to 3 cm height. The plants were randomly arranged in a galvanized iron ring (20 cm height×32 cm diameter) and the spaces between the planter bags were filled with sand. One week later, 1 beetle/plant, therefore 16 beetles per fescue rep was seeded into each ring. The rings were covered with shade cloth stretched over metal hoops and secured by strong elastic. This was replicated 10 times. The trial was maintained in a glasshouse at Ruakura Research Centre, Hamilton where the plants were watered when required.

Damage Assessments

Three weeks post black beetle addition, each plant was assessed for the number of live tillers, tillers with minor damage (small amount feeding) and those severely damaged (tiller very shredded). Each plant was then trimmed down to 3 cm and the herbage was dried and weighed. After a further 2 weeks, the plants were again assessed for tiller damage. The number of live beetles within each planter bag was also recorded at this time.

Data Analysis

The data was analyzed using ANOVA. As there was a difference between treatments in the number of tillers/plant prior to the addition of beetles, damage and dry matter data were analyzed using initial tiller counts as a covariate. This enabled treatments to be compared as if they had the same number of tillers available for black beetle consumption.

Results

Presented here is the comparison between the variety Martin2 with no endophyte and Martin2 with endophyte 647 and the comparison between the variety Tower with no endophyte and Tower with endophyte 647.

Feeding Damage

Feeding damage was easily identified by the degree of shredding at the base of the tillers. Severely damaged tillers were either dead or wilting and could be removed from the plant by gently tugging at the tiller base. If a small amount of feeding damage was visible but the tiller was still healthy, the damage was scored as minor There was no difference in the number of beetles found associated with each treatment (within the planter bag). Black beetle survival was excellent, with between 85% and 100% survival/replicate.

Figure 2:
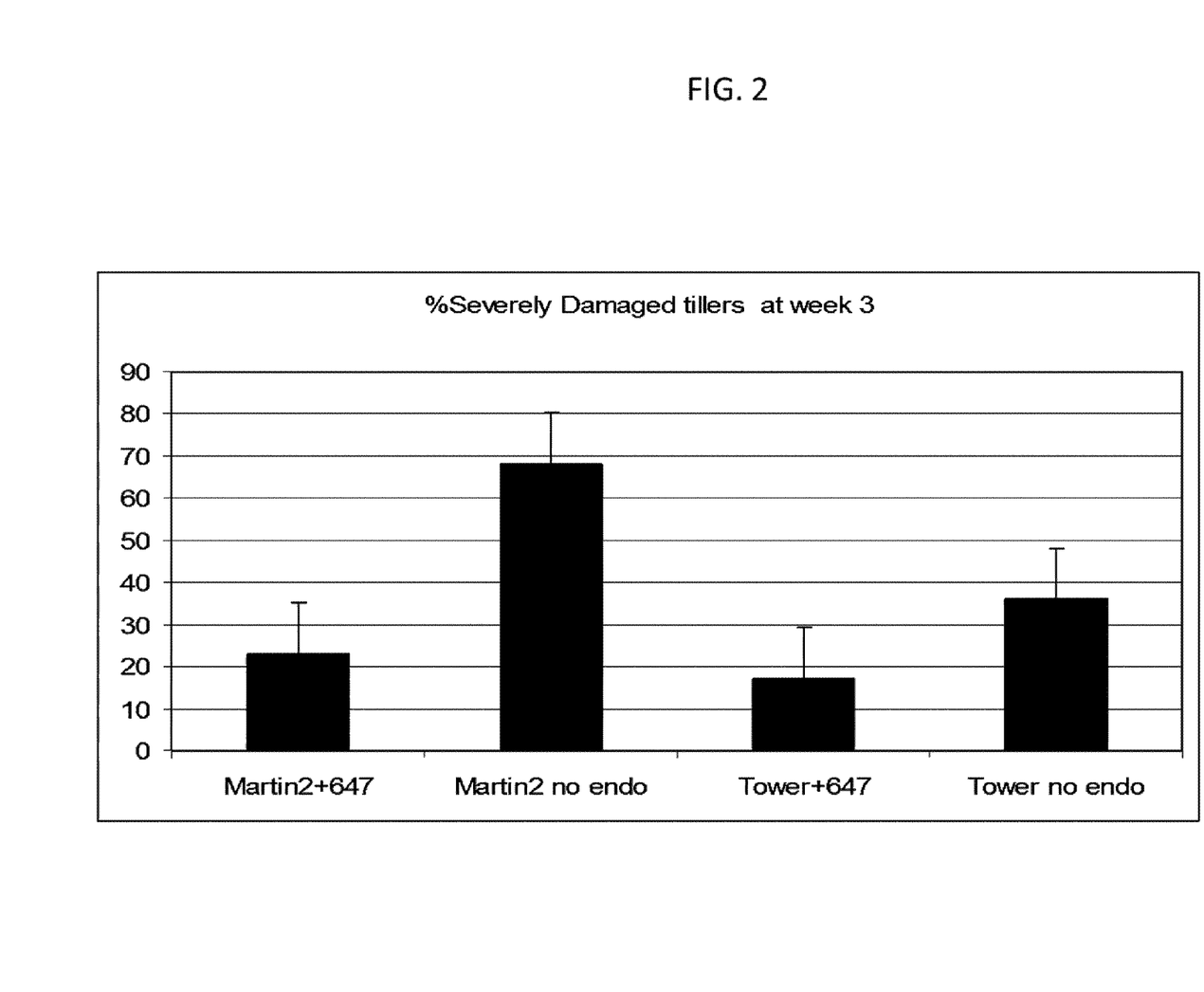
FIG. 2 is a bar graph showing the percentage of tillers that were severely damaged after being caged with black beetle adults for 3 weeks. (P>0.05) LSD 5%=24.2.

At three weeks post black beetle addition, endophyte-infected lines (Martin2+647; Tower+647) had fewer damaged tillers than endophyte-free treatments. Martin2+647 was significant (P<0.001) different to endophyte-free treatment (Martin2 no endo) (FIG. 2 and Table 17).

TABLE 17

% Severely damaged tillers with and without 647 endophytes

| Treatment | % severely damaged tillers at week 3 |
|---|---|
| Martin2 + 647 | 23 |
| Martin2 no endo | 68 |
| Tower + 647 | 17 |
| Tower no endo | 36 |
| LSD 5% | 24 |

Dry Matter

Once the dead tillers were removed, dry matter cuts were taken from the remaining live tillers on each plant. Data were analyzed using initial tiller numbers prior to black beetle addition as a covariate.

Figure 3:
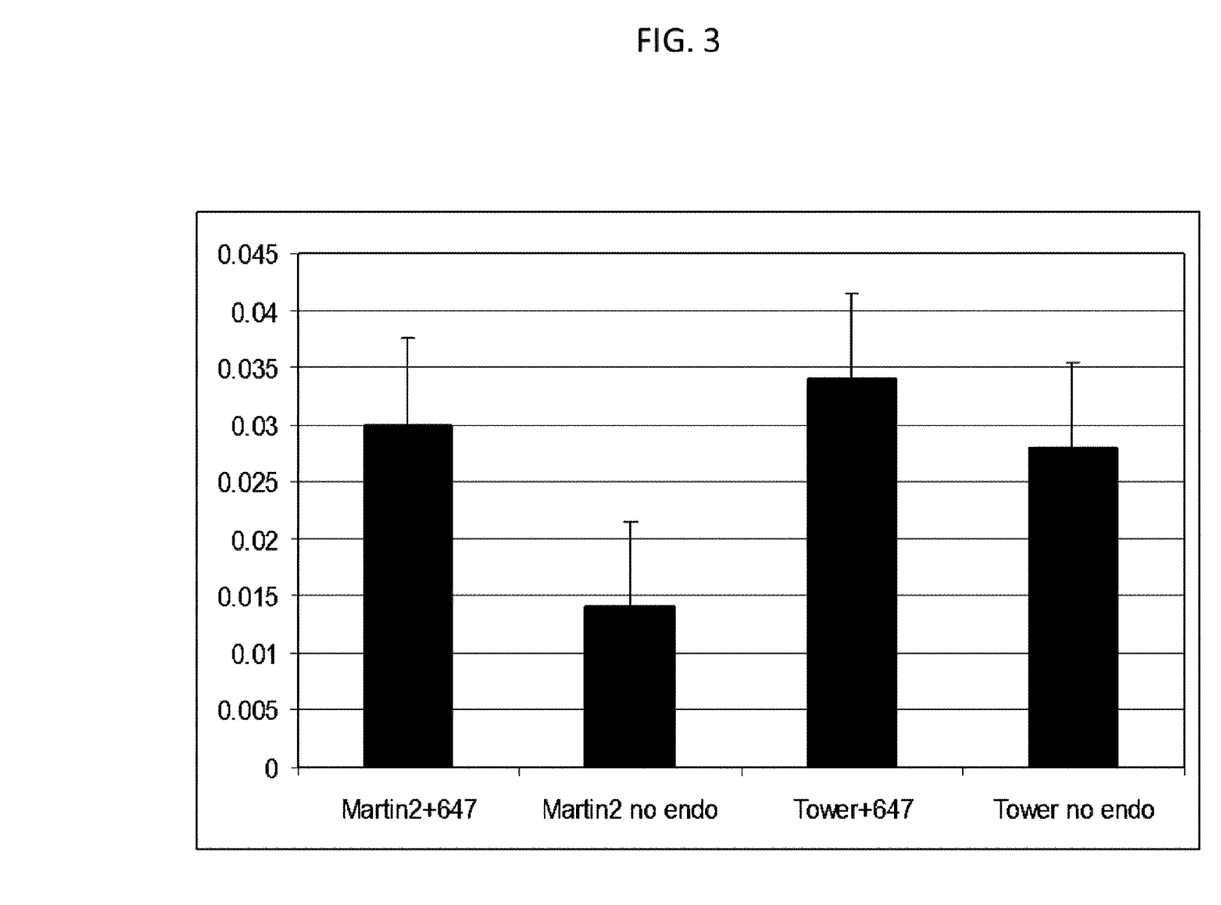
FIG. 3 is a bar graph showing the average dry matter weights (g) of tillers from each fescue treatment after being caged with black beetle adults for 3 weeks. (P>0.05) LSD 5%=0.015.

Endophyte treatments (Martin2+647; Tower+647) had greater average dry weights than endophyte-free treatments. Martin2+647 was significantly (P<0.001) different to endophyte-free treatment (Martin2 no endo) (FIG. 3, Table 18).

TABLE 18

Dry matter of live tillers with and without 647 endophytes

| Treatment | Dry matter of live tillers (g) |
|---|---|
| Martin2 + 647 | 0.030 |
| Martin2 no endo | 0.014 |
| Tower + 647 | 0.034 |
| Tower no endo | 0.028 |
| LSD 5% | 0.015 |

Thus, the new 647 endophyte provides increased resistance to black beetles and can be used to control black beetles. For example, by inoculating grass seeds and grass plants with 647, this provides a grass plant that will have increased resistance to infestation by black beetles, thereby reducing damage to the grass plants.

EXAMPLE 6

Evaluation of Endophyte-Infected Fescue Grasses for Production of Dry Matter in a Field Trial This example expands on the results provided in Example 5, by evaluating dry matter in a field trial.

Materials and Methods

The experiment was sown near Christchurch (43 40 S; 172 33 E), New Zealand on 31 Mar. 2011 into a neutral to alkaline grey clay using a cone seeder. The site receives a mean annual rainfall of 650 mm. The site was under a pea crop the year before the experiment. After harvest the area was cultivated and sprayed with glyphosate to kill weeds. Plot size was 8×1.2 m with a 30 cm buffer between plots. Forty grass/endophyte combinations were arranged in a randomized block design with two replicates.

Presented here is the comparison between the variety Kentucky 31 with no endophyte and Kentucky 31 with the wildtype endophyte and the comparison between the variety Tower with no endophyte and Tower with endophyte 647.

The sowing rate was 20 kg/ha and fertilizer was applied at a rate of 200 kg/ha of "nitrophoska" (NPKS: 12; 5.2; 14.1; 6) at sowing.

Weed control after sowing consisted of a post emergence application of 4 liters/ha of "Nortron" (Ethofumesate containing 500 g/liter of active ingredient) in early winter to kill "*Poa annua*" followed by an application of 1.5 liters/ha of "Jaguar" (25 g/liter diflufenican and 250 g/liter bromoxynil) in early spring to control broad leaf weeds.

The first cut for dry matter production was done on Aug. 2, 2011 using a "Haldrup" plot harvester which cuts the whole plot at a height of 5 cm and weighs the fresh forage. Dry matter was determined by taking sub-samples and drying them in an oven at 100° C. until constant weight. Subsequent cuts were made each time plants reached a standing biomass of more than 1000 kgDM/ha but less than 2500 kgDM/ha. After each cut a light top dressing of 40 kg urea/ha (46% N) was applied. Eleven cuts were taken between sowing and the end of March 2012 and another 11 cuts until 2 Apr. 2013. During summer the trial was irrigated every time the plants showed signs of water stress. No further irrigation will be applied in future to determine the effects of the endophyte symbiosis on drought tolerance. No insect spraying will be applied to make sure of maximum biotic and abiotic stresses are applied on the plants.

Results

Results were analyzed using "Genstat" release 12.1. As shown in Table 19, there was no significant difference yet between the non endophyte infected varieties and their endophyte infected partners in the first year. However, the difference between Tower no endophyte and Tower 647 were almost significant at the 5% level. Differences between treatments with endophytes and their no endophyte counterparts became evident during the second summer with the largest significant differences (p<0.05) shown in the last cut at the end of the summer drought in early April 2013 (Table 19). When the total production for the first two years is examined, significant differences in favor of the treatments containing an endophyte were observed. Since no insecticide was applied and drought conditions were observed in the second summer without applied irrigation, it is concluded that the better performance between treatments was a combination of better drought and insect tolerance in the varieties with endophyte. These results demonstrate a positive effect on the dry matter yield from using endophyte 647. These results are supported by the dry matter yields recorded in the pot trial in Example 5 (FIG. 3 and Table 19).

TABLE 19

Dry matter (kg/DM/ha) of live tillers with and without endophytes

| Variety/endophyte | Production year one | Production 2 Apr. 2013 | Total production |
| --- | --- | --- | --- |
| Kentucky 31 no endophyte | 17427 | 986 | 31283 |
| Kentucky 31 wildtype endophyte | 18061 | 2296 | 35884 |
| Tower + 647 | 21964 | 2677 | 41721 |
| Tower no endophyte | 19984 | 1309 | 36783 |
| LSD | 2148 | 793 | 4218 |

EXAMPLE 7

Inoculation of Other Grasses with 647 Endophyte

The 647 endophyte can also be used to inoculate other grasses, such as other forage grasses, such as tall fescues. Such synthetic combinations of endophyte and grass or endophyte and seed can be used for grazing or for planting in a pasture. For example, the inoculation methods described in Example 1 can be used to inoculate seeds from any desired grass, such as a forage grass (e.g., a tall fescue).

EXAMPLE 8

Genetic Engineering of Endophyte 647

The 647 endophyte described herein can be used as a host for the introduction or deletion of various nucleic acid sequences (for example through the use of recombinant nucleic acid sequences or mutagenesis). For example, the genes responsible for alkaloid biosynthesis can be attenuated through deletion or alteration of their control sequences using the methods described in U.S. Pat. No. 6,335,188, which is herein incorporated by reference.

TABLE 20 primer sequences used in endophyte genotyping

| SEQ ID 1 | Primer B1 |
| --- | --- |
| SEQ ID 2 | Primer B1 |
| SEQ ID 3 | Primer B4 |
| SEQ ID 4 | Primer B4 |
| SEQ ID 5 | Primer B9 |
| SEQ ID 6 | Primer B9 |
| SEQ ID 7 | Primer B9 |
| SEQ ID 8 | Primer B10 |
| SEQ ID 9 | Primer B10 |
| SEQ ID 10 | Primer B11 |
| SEQ ID 11 | Primer B11 |
| SEQ ID 12 | Primer NCESTA1DH04 F |
| SEQ ID 13 | Primer NCESTA1DH04 R |
| SEQ ID 14 | Primer NCESTA1FH03 |
| SEQ ID 15 | Primer NCESTA1FH03 |
| SEQ ID 16 | Primer NCESTA1AG05 |
| SEQ ID 17 | Primer NCESTA1AG05 |
| SEQ ID 18 | Primer NCESTA1IC04 |
| SEQ ID 19 | Primer NCESTA1IC04 |
| SEQ ID 20 | Primer NCESTA1GA07 |
| SEQ ID 21 | Primer NCESTA1GA07 |
| SEQ ID 22 | Primer NCESTA1AG12 |
| SEQ ID 23 | Primer NCESTA1AG12 |
| SEQ ID 24 | Primer NCESTA1FC04 |
| SEQ ID 25 | Primer NCESTA1FC04 |
| SEQ ID 26 | Primer NCESTA1DB06 |
| SEQ ID 27 | Primer NCESTA1DB06 |

REFERENCES

Aldrich et al., 1993. The effects of endophyte-infected tall fescue consumption on diet utilization and thermal regulation in cattle. *J. ANIM. SCI.* 71:164

Arachevaleta, M., C. W. Bacon, C. S. Hoveland, D. E. Radcliffe (1988). Effect of the tall fescue endophyte on plant response to environmental stress. *AGRON. J. Vol.* 81, No 1 83-90.

Ball, D. M., J. F. Pedersen, G. D. Lacefield (1993). *J. ANIM. SCI.* 81,370-379.

Ball, D. M., C. S. Hoveland, and G. D. Lacefield (Forth Edition). 2007 FESCUE TOXCITY. Page 198-205. SOUTHERN FORAGES. Potash and Phosphate Institute. Atlanta, Ga.

Cherney and Johnson, 1993. Tall Fescue for Forage Production. Indiana Ext. Serv., Purdue Univ. AY-98 Rev. 3/93

Christensen et al., 1993. Taxonomy of *Acremonium* endophytes of tall fescue (*Festuca arundinaecea*), meadow fescue (*F. pratensis*), and perennial ryegrass (*Lolium perenne*). Mycol. Res. 97:1083-1092

Gwinn et al., 1991. Tissue print-immunoblot: an accurate method for the detection of *Acremonium coenophialum* in tall fescue. *Phytopathology* 81:747-748.

Hahn et al., 2003. Detection of the endophytic fungi in *Festuca* spp. by means of tissue print immunoassay. *Plant Breeding* 122: 217-222.

Hancock, D. W. 2011. Tall fescue. Georgia Ext. Serv., Univ. of Georgia. CSS-F016.

Hoveland, C. S. 1993. Importance and economic significance of *Acremonium* endophytes to performance of animals and grass plant. Pages 3-12 in R. Joost and S. Quisenberry, ed. *Acremonium*/Grass Interactions. Elsevier, Amsterdam.

Hoveland, C. S., S. P. Schmidt, C. C. King, Jr., J. W. Odom, E. M. Clark, J. A. McGuire, L. A. Smith, H. W. Grimes, and J. L. Holliman 1983. Steer performance and association Johnson-Cicalese J, Secks M E, Lam C K, Meyer W A, Murphy J A, Belanger F C. 2000. Cross species inoculation of Chewings and strong creeping red fescues with fungal endophytes. Crop Science 40, 1485-9.

Lacefield, G. D., J. K. Evans. 1984. TALL FESCUE IN KENTUCKY. University of Kentucky College of Agriculture, Agricultural Communications Services. AGR-108.

Latch et al., 1987. Incidence of endophytes in seeds from collections of *Lolium* and *Festuca* species. Annals of Applied Biology 111:59-64.

Lyons et al., 1986. Occurrence of Peptide and Clavine Ergot Alkaloids in Tall Fescue Grass. *Science,* 232:487-489.

Middendorf et al., 1992. Continuous, online DNA sequencing using a versatile infrared-laser scanner electrophoresis apparatus. *Electrophoresis* 13:487-494.

Moon et al., 1999. Identification of *Epichloë* endophytes in planta by a microsatellite-based PCR fingerprinting assay with automated analysis. *Appl. Environ. Microbiol.* 65:1268-1279.

Parish, J. A., M. A. McCann, R. H. Watson, C. S. Hoveland, L. L. Hawkins, N. S. Hill, J. H. Bouton. 2003. Use of nonergot alkaloid-producing endophytes for alleviating tall fescue toxicosis in sheep. *J. ANIM. SCI.,* 81:1316-1322.

Paterson, J., C. Forcherio, B. Larson, M. Samford and M. Kerley. 1995. The effects of fescue toxicosis on beef cattle productivity. *J ANIM. SCI.* 1995, 73:889-898.

Pedersen et al., 1986. Check year on page 2 year is 1983 Steer performance as affected by tall fescue cultivar and level of *Acremonium coenophialum* infection, *New Zealand J. Exp. Agriculture,* 14:3, 307-312.

Peters et al., 1992. *J. Anim. Sci.,* 70:1550-1561.

Popay, A. J. and S. A. Bonos (2008) Biotic Responses in Endophytic Grasses, in *Neotyphodium* in Cool-Season Grasses (eds C. A. Roberts, C. P. West and D. E. Spiers), Blackwell Publishing Ltd, Oxford, UK. doi: 10.1002/9780470384916.ch7.

Roberts, C. A. (2000). Tall fescue toxicosis. MU Guide, MU Extension, University of Missouri-Columbia. G 4669:1-4.

Schardl et al., 1991. Molecular phylogenetic relationships of nonpathogenic grass mycosymbionts and clavicipitaceous plant pathogens. *Plant Syst. Evol.* 178:27-41.

Schillo et al., 1988. Effects of Endophyte-Infected Fescue on Concentrations of Prolactin in Blood Sera and the Anterior Pituitary and Concentrations of Dopamine and Dopamine Metabolites in Brains of Steers. *J. Anim. Sci.* 66:713-718.

Schmidt, S. P., D. A. Danielson, J. A. Holliman, H. W. Grimes, and W. B. Webster (1986). Alabama Agric. Exp. Stn., Auburn Univ. *Highlights of Agric. Res.* 33:15.

van Zijll de Jong, E., K. M. Guthridge, G. C. Spangenberg and J. W. Forster. 2003. Development and characterization of EST-derived simple sequence repeat (SSR) markers for pasture grass endophytes. *Genome* 46:277-290

West, C. P., and J. C. Waller (2007). Humid transition zone. p. 313-321. In R. F. Barnes et al. (ed.) Forages: The science of grassland agriculture. vol. 2, 6th ed. Blackwell Publ., Ames, Iowa.

Zanzalari, K. P., R. N. Heitmann, J. B. McLaren and H. A. Fribourg. 1989. Effects of endophyte infected fescue and cimetidine on respiration rates, rectal temperatures and hepatic mixed function oxidae activity as measured by hepatic antipyrine metabolism in sheep. *J. ANIM. SCI.,* 67:3370-3378.

In view of the many possible embodiments to which the principles of the disclosure may be applied, it should be recognized that the illustrated embodiments are only examples of the disclosure and should not be taken as limiting the scope of the invention. Rather, the scope of the disclosure is defined by the following claims. We therefore claim as our invention all that comes within the scope and spirit of these claims.

The invention claimed is:

1. An endophyte deposited with The Centraalbureau voor Schimmelcultures (CBS) as Deposit No. CBS 133163 further comprising a recombinant nucleic acid sequence.

2. A synthetic endophyte/grass plant cultivar combination, comprising the endophyte deposited with The Centraalbureau voor Schimmelcultures (CBS) as Deposit No. CBS 133163 and a tall fescue grass plant cultivar.

3. The synthetic endophyte/grass plant cultivar combination of claim 2, which has been made by inoculating the tall fescue grass plant cultivar with the endophyte.

4. The synthetic endophyte/grass plant cultivar combination of claim 2, which has been made by crossing a tall fescue grass plant cultivar comprising the endophyte deposited with The Centraalbureau voor Schimmelcultures (CBS) as Deposit No. CBS 133163 with an endophyte-free grass plant cultivar.

5. Seeds of the synthetic endophyte/grass cultivar combination of claim 2, wherein said seeds comprise the endophyte deposited with The Centraalbureau voor Schimmelcultures (CBS) as Deposit No. CBS 133163.

6. The seeds of claim 5, wherein the seeds have been harvested from tall fescue grass plant cultivars inoculated with the endophyte.

7. The seeds of claim 5, wherein the seeds have been harvested from:
   plants of the synthetic endophytes/grass plant cultivar combination grown from seeds harvested from a grass plant cultivar inoculated with the endophyte, or
   seeds of subsequent generations of grass plant cultivars inoculated with the endophyte.

8. The tall fescue grass plant cultivar of claim 2, wherein the tall fescue plant cultivar is Martin 2, Tower, or IS-FTF 68.

9. A method of increasing the fresh weight yield of a tall fescue cultivar, increasing the dry matter of live tillers of a tall fescue cultivar, reducing black beetle damage to a tall fescue cultivar, or increasing insect resistance in a tall fescue cultivar, comprising:
   inoculating a tall fescue grass plant cultivar or seed with the endophyte deposited with The Centraalbureau voor Schimmelcultures (CBS) as Deposit No. CBS 133163; and
   allowing the grass plant cultivar or seed to grow, thereby increasing the fresh weight yield of the tall fescue cultivar, increasing the dry matter of live tillers of the tall fescue cultivar, reducing black beetle damage to the tall fescue cultivar, or increasing insect resistance in the tall fescue cultivar, as compared to a tall fescue grass plant cultivars without the endophyte.

10. The method of claim 9, wherein the method reduces black beetle damage to the tall fescue cultivar as compared to a tall fescue grass plant cultivar without the endophyte.

11. The method of claim 9, wherein the method increases insect resistance in the tall fescue cultivar as compared to a tall fescue grass plant cultivar without the endophyte.

12. The method of claim 9, wherein increasing insect resistance or reducing black beetle damage to the tall fescue cultivar reduces the amount of severely damaged tillers.

13. The method of claim 9, wherein the method increases the fresh weight yield of the tall fescue cultivar, increases the dry matter of live tillers of the tall fescue cultivar, or both, as compared to a tall fescue grass plant cultivar without the endophyte.

* * * * *